United States Patent
Izawa et al.

(10) Patent No.: US 11,248,205 B2
(45) Date of Patent: Feb. 15, 2022

(54) AROMATIC CULTURE PRODUCT OF MICROORGANISM

(71) Applicant: KABUSHIKI KAISHA YAKULT HONSHA, Minato-ku (JP)

(72) Inventors: Naoki Izawa, Minato-ku (JP); Miyuki Kudo, Minato-ku (JP); Toshiro Sone, Minato-ku (JP)

(73) Assignee: KABUSHIKI KAISHA YAKULT HONSHA, Minato-ku (JP)

(*) Notice: Subject to any disclaimer, the term of this patent is extended or adjusted under 35 U.S.C. 154(b) by 0 days.

(21) Appl. No.: 16/612,128

(22) PCT Filed: Jun. 26, 2017

(86) PCT No.: PCT/JP2017/023444
§ 371 (c)(1),
(2) Date: Nov. 8, 2019

(87) PCT Pub. No.: WO2019/003283
PCT Pub. Date: Jan. 3, 2019

(65) Prior Publication Data
US 2020/0165563 A1    May 28, 2020

(51) Int. Cl.
| | |
|---|---|
| *C12N 1/16* | (2006.01) |
| *A23L 31/10* | (2016.01) |
| *A23L 27/20* | (2016.01) |
| *A61K 8/9728* | (2017.01) |
| *A61K 47/46* | (2006.01) |
| *C12N 1/20* | (2006.01) |
| *C12N 1/14* | (2006.01) |
| *C12R 1/46* | (2006.01) |
| *C12R 1/645* | (2006.01) |

(52) U.S. Cl.
CPC .............. *C12N 1/16* (2013.01); *A23L 27/204* (2016.08); *A23L 31/10* (2016.08); *A61K 8/9728* (2017.08); *A61K 47/46* (2013.01); *C12N 1/20* (2013.01); *C12N 1/145* (2021.05); *C12N 1/205* (2021.05); *C12N 2500/32* (2013.01); *C12R 2001/46* (2021.05); *C12R 2001/645* (2021.05)

(58) Field of Classification Search
CPC .......... C12N 1/16; C12N 1/20; C12N 1/145; C12N 1/205; C12N 2500/32; C12R 2001/46; C12R 2001/2001; A23L 31/10; A23L 27/204; A61K 8/9728; A61K 47/46
See application file for complete search history.

(56) References Cited

U.S. PATENT DOCUMENTS

| | | | | |
|---|---|---|---|---|
| 3,694,232 A | * | 9/1972 | Hall | C07C 45/513 426/538 |
| 8,703,474 B2 | * | 4/2014 | Chang | C12P 7/22 435/255.4 |
| 2018/0000139 A1 | | 1/2018 | Izawa et al. | |

FOREIGN PATENT DOCUMENTS

| | | | | | |
|---|---|---|---|---|---|
| CN | 101948718 A | * | 1/2011 | .............. | C12G 3/02 |
| JP | 5-49465 A | | 3/1993 | | |
| JP | 2001-103959 A | | 4/2001 | | |
| JP | 2004-236638 A | | 8/2004 | | |
| JP | 2007-254313 A | | 10/2007 | | |
| JP | WO 2009/008362 A1 | | 1/2009 | | |
| JP | 2011-83224 A | | 4/2011 | | |
| JP | 2012-55286 A | | 3/2012 | | |
| JP | WO 2016/117489 A1 | | 7/2016 | | |
| TW | 201321504 A1 | | 6/2013 | | |
| WO | WO-2009147157 A1 | * | 12/2009 | ........... | A23C 9/1209 |

OTHER PUBLICATIONS

Tabanelli et al., Survival of the functional yeast Kluyveromyces marxianus B0399 in fermented milk with added sorbic acid, 2016, Journal of Dairy Science, vol. 99 No. 1, pp. 120-129 (Year: 2016).*
International Search Report dated Sep. 19, 2017 in PCT/JP2017/023444 filed Jun. 26, 2017.
Fabre, C. E. et al., "Production of 2-Phenylethyl Alcohol by *Kluyveromyces marxianus*," Biotechnology Progress, vol. 14, No. 2, 1998, pp. 270-274.
Dragone, G. et al., "Characterisation of volatile compounds in an alcoholic beverage produced by whey fermentation," Food Chemistry, vol. 112, 2009, pp. 929-935.
Etschmann, M. M. W. et al., "An aqueous-organic two-phase bioprocess for efficient production of the natural aroma chemicals 2-phenylethanol and 2-phenylethylacetate with yeast," Applied Microbiology and Biotechnology, vol. 71, 2006, pp. 440-443.
Etschmann, M. M. W. et al., "Production of 2-Phenylethanol and 2-Phenylethylacetate from L-Phenylalanine by Coupling Whole-Cell Biocatalysis with Organophilic Pervaporation," Biotechnology and Bioengineering, vol. 92, No. 5, Dec. 5, 2005, pp. 624-634.
Gethins, L. et al., "Influence of carbon and nitrogen source on production of volatile fragrance and flavour metabolites by the yeast *Kluyveromyces marxianus*," Yeast, vol. 32, Nov. 12, 2014, pp. 67-76.
Japanese Office Action dated Dec. 17, 2019, in Patent Application No. 2016/107711, 10 pages (with unedited computer generated English translation).

(Continued)

*Primary Examiner* — Ali Soroush
(74) *Attorney, Agent, or Firm* — Oblon, McClelland, Maier & Neustadt, L.L.P.

(57) ABSTRACT

Provided is a culture product having a mild rose aroma and suitable for imparting the rose aroma to a cosmetic product, a food or a drink, a pharmaceutical product, and the like. A culture product, which is obtained by fermenting a lactic acid bacterium culture product in a medium containing a milk component with *Kluyveromyces marxianus*, and comprises isoamyl alcohol in an amount of 0.3 to 5 parts by mass with respect to 1 part by mass of phenylethyl acetate.

16 Claims, No Drawings

(56) References Cited

OTHER PUBLICATIONS

Singaporean Office Action dated Feb. 11, 2021 in Singaporean Patent Application No. 11201910292Q, 10 pages.
Onur Güşer, et al., "Volatile metabolites produced from agro-industrial wastes by Na-alginate entrapped *Kluyveromyces marxianus*," Brazilian Journal of Microbiology, vol. 47, 2016, pp. 965-972.
Combined Taiwanese Office Action and Search Report dated Jan. 28, 2021 in Patent Application No. 106122134 (with English machine translation), 13 pages.

* cited by examiner

AROMATIC CULTURE PRODUCT OF MICROORGANISM

TECHNICAL FIELD

The present invention relates to a microorganism culture product having a rose aroma and its use.

BACKGROUND ART

2-Phenylethanol (2PE) and phenylethyl acetate (PEAc) are known as typical rose aroma components. Such compounds are generally chemically synthesized and used in the flavoring of various commodities including cosmetic products.

However, since the aroma of these chemical synthetics is monotonous and strongly irritating, a milder and more natural aroma has been demanded. Further, there is a concern that the solvent used in the synthesis may remain.

In addition, it is known that certain types of yeast such as *Saccharomyces cerevisiae* produce an aroma component, and the culture products have been used as aromatic culture products for food, drink, or the like (Patent Literatures 1 to 3).

*Kluyveromyces marxianus* is known as a yeast producing 2-phenylethanol, and it has been reported that 2-phenylethanol can be efficiently produced by culturing the yeast in a medium added with L-phenylalanine, which is a precursor (Non Patent Literature 1). However, when the culture is performed using a common yeast medium, it is difficult to use the culture product as it is for cosmetic products or the like because of the strong odor of yeast extract, peptone, or the like contained in the medium, and it is necessary to perform a distillation treatment or isolate and purify 2-phenylethanol.

Meanwhile, it has been reported that alcoholic beverages can be produced by distilling a fermented liquid obtained by fermenting cheese whey with *Kluyveromyces marxianus* ATCC10022, and that the distillate contains volatile components such as ethyl acetate in addition to alcohols such as isoamyl alcohol, isobutyl alcohol, 1-propanol, and isopentyl alcohol (Non Patent Literature 2).

CITATION LIST

Patent Literature

Patent Literature 1: JP-A-5-49465
Patent Literature 2: JP-A-2001-103959
Patent Literature 3: JP-A-2012-55286

Non Patent Literature

Non Patent Literature 1: CE Fabre et al., Biotechnol. Prog. 14, 270-274 (1998)
Non Patent Literature 2: G. Dragone et al., Food Chemistry 112, 929-935 (2009)

SUMMARY OF THE INVENTION

Technical Problem

The present invention relates to providing a microorganism culture product having a mild rose aroma and suitable for imparting the rose to a cosmetic product, a food or a drink, a pharmaceutical product, and the like.

Solution to Problem

The present inventors carried out extensive studies to develop a composition having a good rose aroma, and found that a culture product obtained by fermenting a lactic acid bacterium culture product in a medium containing a milk component with *Kluyveromyces marxianus* exhibits a gorgeous and mild rose aroma instead of an alcohol odor, and is useful for imparting the aroma to a cosmetic product, a food or a drink, a pharmaceutical product, and the like, thereby completing the present invention.

That is, the present invention relates to the following [1] to [14].
[1] A culture product, which is obtained by fermenting a lactic acid bacterium culture product in a medium containing a milk component with *Kluyveromyces marxianus*, and comprises isoamyl alcohol in an amount of 0.3 to 5 parts by mass with respect to 1 part by mass of phenylethyl acetate.
[2] The culture product according to [1], wherein the fermentation is performed in the presence of L-phenylalanine.
[3] The culture product according to [1] or [2], wherein the milk component is skim milk powder.
[4] The culture product according to any of [1] to [3], wherein the lactic acid bacterium culture product is a culture supernatant.
[5] The culture product according to any of [1] to [4], wherein the *Kluyveromyces marxianus* is *Kluyveromyces marxianus* YIT12612 (NBRC0260).
[6] The culture product according to any of [1] to [5], wherein the lactic acid bacterium is *Streptococcus thermophilus* YIT2084 (FERM BP-10879).
[7] The culture product according to any of [1] to [6], wherein the fermentation is performed by adding the *Kluyveromyces marxianus* to the lactic acid bacterium culture product in a medium containing a milk component, followed by culture at 15 to 45° C. for 15 to 54 hours.
[8] The culture product according to any of [1] to [7], wherein the culture product is a distillate subjected to a distillation treatment.
[9] A flavoring composition, comprising the culture product according to any of [1] to [8].
[10] A cosmetic product, comprising the culture product according to any of [1] to [8].
[11] A food or a drink, comprising the culture product according to any of [1] to [8].
[12] A pharmaceutical product, comprising the culture product according to any of [1] to [8].
[13] A method for imparting a rose aroma to a cosmetic product, a food or a drink, or a pharmaceutical product, comprising adding the culture product according to any of [1] to [8] thereto.
[14] A method for producing a culture product comprising isoamyl alcohol in an amount of 0.3 to 5 parts by mass with respect to 1 part by mass of phenylethyl acetate, comprising fermenting a lactic acid bacterium culture product in a medium containing a milk component with *Kluyveromyces marxianus*.

Advantageous Effects of Invention

The culture product of the present invention exhibits a milder rose aroma than chemical synthetics and is useful as a flavoring composition for imparting a high quality and mild rose aroma to a cosmetic product, a food or a drink, a pharmaceutical product, and the like.

DESCRIPTION OF EMBODIMENTS

The culture product of the present invention is a culture product which is obtained by fermenting a lactic acid bacterium culture product in a medium containing a milk component with *Kluyveromyces marxianus*, and comprises isoamyl alcohol in an amount of 0.3 to 5 parts by mass with respect to 1 part by mass of phenylethyl acetate.

In the present invention, the term "milk component" means raw milk, heat-treated milk, skim milk powder, or whole milk powder of animal's milk such as cow milk, goat milk, and sheep milk, or a material containing a milk-derived component such as fresh cream and whey. Among these, skim milk powder is preferable. The "whey" is obtained by removing fat and casein from the milk components.

In the present invention, as the lactic acid bacterium culture product in a medium containing a milk component, for example, a culture product obtained by culturing a lactic acid bacterium in a medium containing the above-mentioned milk component (a milk component-containing medium) may be mentioned, and a culture supernatant of the culture product may suitably be mentioned. Fermentation of the milk component-containing medium with microorganisms not only suppresses odors derived from the milk components and hardly affects a mild rose aroma, but also lowers the pH, thereby precipitating insoluble components derived from the milk components and increasing the work efficiency when a culture supernatant is obtained.

The milk component-containing medium may further contain other components such as sugars, vitamins, degraded products of proteins, amino acids, minerals, salts, surfactants, fatty acids, and metals. The other components are not particularly limited, but sugars such as glucose, galactose, lactose, and fructose are preferable. Glucose is particularly preferable as the sugar in view of its utilization by microorganisms. The yeast extract, peptone, and the like are preferably not used because they may affect the aroma of the culture product of the present invention.

The content of the milk component in the medium is not particularly limited, but is preferably 1 to 50% by mass (hereinafter, when simply referred to as "%", it indicates "% by mass"), and more preferably 2 to 10% in terms of solid content. The content of glucose is preferably 0.1 to 10%, and more preferably 1 to 5% from the viewpoint of growth ability of microorganisms.

Herein, examples of the lactic acid bacterium include a *Lactbacillus* bacterium such as *Lactobacillus casei*, *Lactobacillus mali*, *Lactobacillus acidophilus*, *Lactobacillus delbrueckii* subsp. *bulgaricus*, and *Lactobacillus helveticus*; a *Streptococcus* bacterium such as *Streptococcus thermophilus*; a *Lactococcus* bacterium such as *Lactococcus lactis* subsp. *lactis* and *Lactococcus lactis* subsp. *cremoris*; an *Enterococcus* bacterium such as *Enterococcus faecalis*; and a *Bifidobacterium* bacterium such as *Bifidobacterium breve*, *Bifidobacterium bifidum*, and *Bifidobacterium longum*. Among these, the *Streptococcus* bacterium is preferable, *Streptococcus thermophilus* is more preferable, and *Streptococcus thermophilus* YIT2084 ('ERM BP-10879) is even more preferable.

The conditions for fermenting the above-mentioned milk component-containing medium with a lactic acid bacterium are not particularly limited, and for example, a lactic acid bacterium may be inoculated into the medium at 0.01 to 10%, preferably at 0.1 to 5%, and the culture may be performed at 20 to 45° C., preferably at 37 to 42° C., for 1 to 48 hours, preferably for 4 to 30 hours. As other culture conditions at this time, standing, stirring, shaking, aeration, and the like may be mentioned, and a method suitable for culturing may be appropriately selected from these.

The lactic acid bacterium culture product in the milk-component containing medium thus obtained can be used as it is, but known purification and separation treatments such as filtration, dialysis, precipitation, and centrifugation can also be performed.

The lactic acid bacterium culture product in the milk component-containing medium used in the present invention is preferably a culture supernatant obtained by fermenting a medium containing skim milk powder with *Streptococcus thermophilus* YIT2084 and removing bacterial cells therefrom, and more preferably a fraction having a molecular weight of 20,000 or less obtained by subjecting the culture supernatant to a treatment such as ultrafiltration, gel filtration, or dialysis. Further, the lactic acid bacterium culture product in the milk component-containing medium preferably comprises a sugar such as lactose or galactose, an amino acid, lactic acid, a protein, or the like.

The culture product of the present invention is prepared by fermenting the lactic acid bacterium culture product in the milk component-containing medium with *Kluyveromyces marxianus*.

Herein, *Kluyveromyces marxianus* is not particularly limited as long as it produces phenylethyl acetate and isoamyl alcohol, but is preferably *Kluyveromyces marxianus* YIT12612 (NBRC 0260).

*Kluyveromyces marxianus* is inoculated preferably at 0.1 to 3.0%, more preferably at 0.2 to 1.0%, relative to the lactic acid bacterium culture product.

At this time, L-phenylalanine (L-phe) is preferably added. The addition of L-phenylalanine can increase the production amounts of phenylethyl acetate and 2-phenylethanol. In this instance, L-phenylalanine is added to the lactic acid bacterium culture product preferably at 0.3 to 10 g/L, more preferably at 0.5 to 5 g/L, and even more preferably at 2 to 4 g/L.

The culture is preferably performed under conditions that do not result in anaerobic conditions, from the viewpoint of increasing the production amounts of phenylethyl acetate and 2-phenylethanol.

The culture temperature is preferably 15 to 45° C., more preferably 20 to 40° C., and even more preferably 30 to 35° C. in view of the production amounts of phenylethyl acetate and isoamyl alcohol and the aroma. The culture time is preferably 1 to 72 hours, more preferably 15 to 54 hours, even more preferably 15 to 48 hours, and particularly preferably 20 to 30 hours. More suitable conditions are at 30 to 35° C. for 20 to 30 hours.

The culture method is not particularly limited, and any of agitation culture, static culture, shaking culture, culture at neutral pH, and the like may be used.

The culture product thus obtained exhibits a mild rose aroma as compared to chemically synthesized phenylethyl acetate because it comprises various aroma components. The culture product can be used as it is as a flavoring composition for imparting the aroma, but it is preferable to use the culture product after removing bacterial cells by filtration, centrifugation, or the like, and it is more preferable to use a distillate obtained by distilling and concentrating the culture product by an atmospheric distillation method, a vacuum distillation method, or the like.

The culture product of the present invention comprises not only phenylethyl acetate and 2-phenylethanol, which are rose aroma components, but also isoamyl alcohol and the like, but from the viewpoint of having a gorgeous and mild rose aroma, the content ratio of phenylethyl acetate and isoamyl alcohol in the culture product is 0.3 to 5 parts by mass, preferably 0.3 to 3 parts by mass, more preferably 0.3 to 1.5 parts by mass of isoamyl alcohol with respect to 1 part by mass of phenylethyl acetate.

Phenylethyl acetate has a more gorgeous rose aroma than 2-phenylethanol. The rose aroma of the culture product of the present invention is based on the rose aroma of phenylethyl acetate and is milder than the aroma of phenylethyl acetate itself.

In addition, the culture product (before distillation) of the present invention preferably comprises phenylethyl acetate in an amount of 10 to 100 ppm, 2-phenylethanol in an amount of 100 to 1500 ppm, and isoamyl alcohol in an amount of 5 to 50 ppm, and the distillate preferably comprises phenylethyl acetate in an amount of 30 to 500 ppm, 2-phenyl ethanol in an amount of 20 to 1200 ppm, and isoamyl alcohol in an amount of 20 to 300 ppm.

Since the culture product of the present invention has a gorgeous and mild rose aroma, it can be used for a flavoring composition, a cosmetic product, a food or a drink, a pharmaceutical product, and the like. In the field of cosmetics, there are few perfumes derived from organisms and industrially available, and the demand for natural perfumes is higher than that for synthetic perfumes, thus the culture product of the present invention can be suitably used for a cosmetic product.

Herein, examples of the cosmetic product include an aromatic cosmetic product such as a perfume, an eau de cologne, or an eau de toilette; a basic cosmetic product such as a toner, a milky lotion, a lotion, a cream, a facial mask, or a serum; a haircare product such as a shampoo or a conditioner; a bath cosmetic product such as a bath agent; a makeup cosmetic product such as a foundation; and a special cosmetic product such as a sunscreen. Examples of the food or the drink include various types of refreshing drinks, a sparkling liquor, a beer, a refined sake, confectionery, an ice, an ice cream, and a dairy product such as fermented milk. Examples of the pharmaceutical product include an external preparation such as a cream, an ointment, and a gel.

The content of the culture product of the present invention in such a cosmetic product, a food or a drink, and a pharmaceutical product is preferably 0.1 to 50 ppm and more preferably 0.1 to 10 ppm in terms of phenylethyl acetate.

EXAMPLES

Next, the present invention will be explained in detail by way of Examples.

Example 1

(1) Preparation of lactic acid bacterium culture product
Streptococcus thermophilus YIT2084 (FERM BP-10879) was inoculated at 1% into a medium containing 3% skim milk powder and statically cultured at 40° C. for 24 hours. The resulting culture product was centrifuged at 8,000×g at 4° C. for 15 minutes. The obtained supernatant was ultrafiltered with a centrifugal ultrafiltration filter (Centricut Mini V-20, manufactured by Kurabo Industries Ltd.) having a cut-off molecular weight of 20,000 Da at 3,000×g at 4° C. for 1 hour to obtain a low molecular weight fraction (molecular weight of not more than 20,000) of the supernatant of the lactic acid bacterium culture product.

As a result of analyzing the low molecular weight fraction, it was found to contain 1.1% lactose, 0.4% galactose, and 0.4% lactic acid, and have a pH of 4.0.

(2) Preparation of *Kluyveromyces marxianus* culture product (a) Strain used

*Kluyveromyces marxianus* YIT12612 (NBRC 0260).

(b) Pre-preculture

Twenty μL of YIT12612 cryopreserved in 20% glycerol was inoculated into 2 mL of Yeast and Mold (YM) medium (1% glucose, 0.5% peptone, 0.3% yeast extract, and 0.3% malt extract), and shaking culture was performed at 160 rpm at 35° C. for 24 hours.

(c) Preculture

Ten mL of the lactic acid bacterium culture product prepared in (1) above was placed in a 50 mL Erlenmeyer flask, the culture product obtained by the pre-preculture in (b) above was inoculated thereinto at 1%, and shaking culture was performed at 160 rpm at 35° C. for 24 hours.

(d) Culture

The culture solution obtained by the preculture in (c) above was inoculated at 0.3% into the lactic acid bacterium culture product prepared in (1) above, and shaking culture was performed at 200 rpm at 35° C. for 48 hours. Separately, L-phenylalanine was added to the lactic acid bacterium culture product prepared in (1) above at 3 g/L, followed by filtration sterilization, and 100 ml of the resultant was added to an autoclaved 8-channel mini-jar fermenter (Bio Jr. 8), thereafter, the culture solution obtained by the preculture in (c) above was inoculated thereinto at 0.3%, and shaking culture was performed at 200 rpm at 35° C. for 24 hours or 48 hours.

After completion of the culture, the following operations were performed to prepare samples (A and B) for analysis of aroma components.

Sample A: the culture product was centrifuged at 15,000 rpm for 10 minutes, to thereby obtain a supernatant.

Sample B: the culture product was subjected to distillation using an evaporator under the conditions where reduction of pressure was started at a heating temperature of 40° C. and a cooling temperature of 0° C. and the distillation was continued at 50 to 60 mbar until about ⅙ of the culture solution was recovered, to thereby obtain a distillate.

(e) Analysis of aroma components and evaluation of aroma

Two mL of each of samples A and B prepared in (d) above was taken in a 2 mL vial, and the aroma components in the sample were quantified by HS-GC-Flame Ionization Detector (FID) (Tables 1 and 2).

Furthermore, sensory evaluation of the aroma of each sample was performed by a specialized panelist. The results are also shown in Table 3.

TABLE 1

| Head Space Conditions | |
|---|---|
| Device | Agilent 7697A |
| Loop size (mL) | 5 |
| Oven temperature (° C.) | 50 |
| Loop temperature (° C.) | 110 |
| Transfer line temperature (° C.) | 115 |
| Vial equilibration (min) | 15 |
| Injection time (min) | 1 |

TABLE 2

| Gas Chromatography Conditions | |
| --- | --- |
| System | Agilent 7890B |
| Column | InertCap Pure WAX 30 m × 0.25 mm i.d. × 0.25 μm (GL Sciences) |
| Oven temperature | 40° C. (5 min)–10° C./min–250° C. (3 min) |
| Carrier gas | He |
| Flow rate | 3 mL/min |
| Injection temperature | 250° C. |
| Split ratio | 20:1 |
| Split flow rate | 60 ml/min |
| Vial equilibration (min) | 5 |
| Injection time (min) | 1 |

TABLE 3

| | Non-addition of L-Phe | | Addition of L-Phe | | | |
| --- | --- | --- | --- | --- | --- | --- |
| | Culture for 48 hours | | Culture for 24 hours | | Culture for 48 hours | |
| | Example Product 1 | Example Product 2 | Example Product 3 | Example Product 4 | Example Product 5 | Example Product 6 |
| Compound (ppm) | Sample A (Culture product) | Sample B (Distillate) | Sample A (Culture product) | Sample B (Distillate) | Sample A (Culture product) | Sample B (Distillate) |
| Phenylethyl acetate | 12.03 | 48.62 | 19.02 | 63.16 | 64.67 | 320.64 |
| 2-Phenylethanol | 143.21 | 30.77 | 219.12 | 72.44 | 582.05 | 305.25 |
| Isoamyl alcohol | 28.08 | 161.82 | 11.42 | 79.14 | 26.61 | 141.46 |
| Phenylethyl acetate: isoamyl alcohol | 1:2.3 | 1:3.3 | 1:0.6 | 1:1.3 | 1:0.4 | 1:0.4 |
| Sensory evaluation | A mild rose aroma was detected hut a fermentation odor was detected. | A slightly weak and mild rose aroma was detected hut a fermentation odor was slightly detected. | A slightly weak and mild rose aroma was detected hut a fermentation odor was slightly detected. | A mild rose aroma was detected and almost no fermentation odor was detected. | A slightly weak and mild rose aroma was detected but a fermentation odor was detected. | A mild rose aroma was detected but a fermentation odor was slightly detected. |

The distillation increased phenylethyl acetate and isoamyl alcohol and decreased 2-phenylethanol, but the ratio of phenylethyl acetate to isoamyl alcohol was approximately 1:0.4 to 3 before and after the distillation. Sample A (culture product) and sample B (distillate) exhibited a mild rose aroma, and the fermented odor was in such a degree that the sample can be used as it is for a cosmetic product. In addition, it was confirmed that the fermentation odor was more suppressed in the case of the culture for 24 hours. It was also confirmed that the addition of phenylalanine increased the production amount of phenylethyl acetate.

Example 2

The sensory evaluation of the aroma of the samples was carried out by three specialized panelists for Example Product 4 of Example 1 and the synthetic products of phenylethyl acetate and isoamyl alcohol. The results are also shown in Table 4.
<Evaluation>
  5: A mild rose aroma is detected.
  4: A mild rose aroma is detected but is slightly irritating or slightly weak as compared to "5".
  3: A rose aroma is detected but is irritating or weak as compared to "5".
  2: A rose aroma is detected but is very irritating or weak as compared to "5".
  1: No rose aroma is detected.

TABLE 4

| | Example Product 4 | Comparative Product 1 | Comparative Product 2 | Comparative Product 3 | Comparative Product 4 |
| --- | --- | --- | --- | --- | --- |
| Compound (ppm) | Sample B (Distillate) | Synthetic product | Synthetic product | Synthetic product | Synthetic product |
| Phenylethyl acetate | 63.16 | 63 | 63 | 63 | 63 |
| Isoamyl alcohol | 79.14 | — | 79 | 6.3 | 630 |
| Phenylethyl acetate: isoamyl alcohol | 1:1.3 | — | 1:1.3 | 1:0.1 | 1:10 |
| Evaluation | 5 | 2.3 | 4 | 3 | 1.3 |
| Comment by specialized panelist | A mild rose aroma was detected and almost no fermentation | A rose aroma was detected but was irritating as compared with Example Product 4. | A rose aroma was detected but its mildness did not last, resulting in a sharp aroma | An aroma was weak as a whole as compared to Example Product 4. | A sake-like odor was strongly detected. The odor was not recognized as a |

TABLE 4-continued

| | Example Product 4 | Comparative Product 1 | Comparative Product 2 | Comparative Product 3 | Comparative Product 4 |
|---|---|---|---|---|---|
| | odor was detected. | | as compared with Example Product 4. | | rose aroma. |

The synthetic phenylethyl acetate was found to have a strongly irritating rose aroma as compared to Example Product 4. When the ratio of phenylethyl acetate to isoamyl alcohol fell outside the range of 1:0.3 to 5, the result was that the rose aroma was weak or that the odor of alcohol was strong. Furthermore, even when the synthetic phenylethyl acetate and the synthetic isoamyl alcohol were blended in a ratio of 1:1.3, the resultant aroma was irritating as compared to Example Product 4, and thus it was confirmed that other components obtained by fermentation also contribute to the mild rose aroma.

Production Example 1

A toner was prepared with the following composition. In the preparation method, (5) and (6) were mixed, (1) to (4) were added thereto, and the mixture was stirred thoroughly to obtain a toner. The toner had a gorgeous and mild rose aroma.

TABLE 5

| | Raw material | Amount used (%) |
|---|---|---|
| (1) | Ethanol | 5.0 |
| (2) | 1,3-Butylene glycol | 2.0 |
| (3) | Polyoxyethylene hydrogenated castor oil | 0.05 |
| (4) | Methyl parahydroxybenzoate | 0.1 |
| (5) | Culture product of Example Product 3 or distillate of Example Product 4 | 10.0* |
| (6) | Distilled water | Balance to 100 |

*The culture product contained 19.02 ppm of phenylethyl acetate, and consequently the cosmetic product contained 1.9 ppm of phenylethyl acetate; and the distillate contained 63.16 ppm of phenylethyl acetate, and consequently the cosmetic product contained 6.3 ppm of phenylethyl acetate.

Production Example 2

A milky lotion was prepared with the following composition. In the preparation method, (7) to (8) were added to (10), the mixture was heated and then emulsified by adding (1) to (6) at 80° C., the mixture was allowed to cool to room temperature, and then (9) was added thereto to obtain a milky lotion. The milky lotion had a gorgeous and mild rose aroma.

TABLE 6

| | Raw material | Amount used (%) |
|---|---|---|
| (1) | Stearic acid | 2.0 |
| (2) | Liquid paraffin | 5.0 |
| (3) | Squalane | 2.0 |
| (4) | Sorbitan monostearate | 0.05 |
| (5) | Polyoxyethylene (20) sorbitan monostearate | 2.0 |
| (6) | Butyl parahydroxybenzoate | 0.05 |
| (7) | Glycerin | 2.0 |
| (8) | Methyl parahydroxybenzoate | 0.1 |

TABLE 6-continued

| | Raw material | Amount used (%) |
|---|---|---|
| (9) | Culture product of Example Product 3 or distillate of Example Product 4 | 3.0* |
| (10) | Distilled water | Balance to 100% |

*The culture product contained 19.02 ppm of phenylethyl acetate, and consequently the cosmetic product contained 0.57 ppm of phenylethyl acetate; and the distillate contained 63.16 ppm of phenylethyl acetate, and consequently the cosmetic product contained 1.9 ppm of phenylethyl acetate.

Production Example 3

A cream was prepared with the following composition. In the preparation method, (9) to (10) were added to (12), the mixture was heated and then emulsified by adding (1) to (8) thereto at 80° C., the mixture was allowed to cool to room temperature, and then (11) was added thereto to obtain a cream. The cream had a gorgeous and mild rose aroma.

TABLE 7

| | Raw material | Amount used (%) |
|---|---|---|
| (1) | Liquid paraffin | 23.0 |
| (2) | Petrolatum | 7.0 |
| (3) | Cetanol | 1.0 |
| (4) | Stearic acid | 2.0 |
| (5) | Beeswax | 2.0 |
| (6) | Sorbitan monostearate | 3.5 |
| (7) | Polyoxyethylene (20) sorbitan monostearate | 2.5 |
| (8) | Butyl parahydroxybenzoate | 0.05 |
| (9) | 1,3-Butylene glycol | 1.0 |
| (10) | Methyl parahydroxybenzoate | 0.1 |
| (11) | Culture product of Example Product 3 or distillate of Example Product 4 | 3.0* |
| (12) | Distilled water | Balance to 100 |

*The culture product contained 19.02 ppm of phenylethyl acetate, and consequently the cosmetic product contained 0.57 ppm of phenylethyl acetate; and the distillate contained 63.16 ppm of phenylethyl acetate, and consequently the cosmetic product contained 1.9 ppm of phenylethyl acetate.

The invention claimed is:

1. A fermentation culture product, which is obtained by fermenting a lactic acid bacterium culture product with *Kluyveromyces marxianus*,
   wherein the lactic acid bacterium culture product is produced by culturing a lactic acid bacterium in a medium comprising a milk component,
   wherein the lactic acid bacterium is *Streptococcus thermophilus* YIT2084 (FERM BP-10879) and the *Kluyveromyces marxianus* is *Kluyveromyces marxianus* YIT12612 (NBRC0260),
   wherein the fermentation is performed in the presence of L-phenylalanine,
   wherein the culture product comprises isoamyl alcohol in an amount of 5 to 50 ppm and phenylethyl acetate in an amount of 10 to 100 ppm, and
   wherein the isoamyl alcohol is present in an amount of 0.3 to 1.5 parts by mass with respect to 1 part by mass of phenylethyl acetate.

2. The fermentation culture product according to claim 1, wherein the milk component is skim milk powder.

3. The fermentation culture product according to claim 1, wherein the lactic acid bacterium culture product is a culture supernatant.

4. The fermentation culture product according to claim 1, wherein the fermentation is performed by adding the *Kluyveromyces marxianus* to the lactic acid bacterium culture product, followed by culture at 15 to 45° C. for 15 to 54 hours.

5. A method of producing a distillate from a fermentation culture product, comprising:
   distilling the fermentation culture product of claim 1 to produce a distillate,
   wherein the distillate comprises isoamyl alcohol in an amount of 20 to 300 ppm and phenylethyl acetate in an amount of 30 to 500 ppm.

6. A method, comprising imparting a rose aroma to a cosmetic product, a food or a drink, or a pharmaceutical product by adding the fermentation culture product according to claim 1 to the cosmetic product, the food or the drink, or the pharmaceutical product.

7. A method for producing a fermentation culture product, comprising:
   culturing a lactic acid bacterium in a medium comprising a milk component to produce an inoculated medium;
   removing the lactic acid bacterium cells from the inoculated medium to produce a lactic acid bacterium culture product; and
   fermenting the lactic acid bacterium culture product with *Kluyveromyces marxianus* in the presence of L-phenylalanine to produce the fermentation culture product,
   wherein the lactic acid bacterium is *Streptococcus thennophilus* YIT2084 (FERM BP-10879) and the *Kluyveromyces marxianus* is *Kluyveromyces marxianus* YIT12612 (NBRC0260),
   wherein the fermentation culture product comprises isoamyl alcohol in an amount of 0.3 to 5 parts by mass with respect to 1 part by mass of phenylethyl acetate.

8. The method of claim 7, wherein the fermentation culture product comprises isoamyl alcohol in an amount of 0.3 to 1.5 parts by mass with respect to 1 part by mass of phenylethyl acetate.

9. The method of claim 7, wherein the milk component is skim milk powder.

10. The method of claim 7, wherein the removing of the lactic acid bacterium cells from the inoculated medium forms a culture supernatant, and the method further comprises subjecting the culture supernatant to ultrafiltration, gel filtration, or dialysis to produce a fraction having a molecular weight of 20,000 or less as the lactic acid bacterium culture product.

11. The method of claim 7, wherein the fermenting comprises: adding the *Kluyveromyces marxianus* to the lactic acid bacterium culture product and maintaining at 15 to 45° C. for 15 to 54 hours.

12. The method of claim 7, further comprising distilling the culture product.

13. The method of claim 12, wherein the distilling produces a distillate, the distillate comprising isoamyl alcohol in an amount of 20 to 300 ppm and phenylethyl acetate in an amount of 30 to 500 ppm.

14. The method of claim 7, further comprising adding the culture product to a cosmetic product.

15. The method of claim 7, further comprising adding the culture product to a food or a drink.

16. The method of claim 7, further comprising adding the culture product to a pharmaceutical product.

* * * * *